United States Patent
Cho et al.

(10) Patent No.: US 9,603,521 B2
(45) Date of Patent: Mar. 28, 2017

(54) MEDICAL MEASURING DEVICE

(75) Inventors: Ok Kyung Cho, Schwerte (DE); Yoon Ok Kim, Schwerte (DE)

(73) Assignee: Ingo Flore, Dortmund (DE)

( * ) Notice: Subject to any disclaimer, the term of this patent is extended or adjusted under 35 U.S.C. 154(b) by 622 days.

(21) Appl. No.: 12/312,730

(22) PCT Filed: Nov. 23, 2007

(86) PCT No.: PCT/EP2007/010207
§ 371 (c)(1),
(2), (4) Date: Aug. 7, 2009

(87) PCT Pub. No.: WO2008/061788
PCT Pub. Date: May 29, 2008

(65) Prior Publication Data
US 2010/0056880 A1  Mar. 4, 2010

(30) Foreign Application Priority Data

Nov. 23, 2006 (DE) .......... 10 2006 055 691
Sep. 7, 2007 (DE) .......... 10 2007 042 550
Sep. 7, 2007 (DE) .......... 10 2007 042 551

(51) Int. Cl.
*A61B 5/1455* (2006.01)
*A61B 5/00* (2006.01)
(Continued)

(52) U.S. Cl.
CPC ......... *A61B 5/00* (2013.01); *A61B 5/01* (2013.01); *A61B 5/02* (2013.01); *A61B 5/022* (2013.01);
(Continued)

(58) Field of Classification Search
CPC . A61B 5/1455; A61B 5/14532; A61B 5/0002; A61B 5/0059; A61B 5/14551; A61B 5/14552
(Continued)

(56) References Cited

U.S. PATENT DOCUMENTS 3,229,686 A   1/1966  Edmark, Jr.
3,805,795 A   4/1974  Denniston et al.
(Continued)

FOREIGN PATENT DOCUMENTS

DE    35 33 912     4/1987
DE    195 19 125    11/1996
(Continued)

OTHER PUBLICATIONS

International Search Report.
(Continued)

*Primary Examiner* — Eric Winakur
*Assistant Examiner* — Chu Chuan (J J) Liu
(74) *Attorney, Agent, or Firm* — Collard & Roe, P.C.

(57) ABSTRACT

A measuring device for non-invasive determination of at least one physiological parameter includes at least one diagnostic sensor unit to generate measuring signals, and an evaluation unit for processing of measuring signals. The diagnostic sensor unit is integrated into or connectible to the keyboard of a computer or into a mobile device of entertainment or communication technology, with the diagnostic sensor unit including: an optical measuring unit including at least one radiation source for irradiation of the examined body tissue and at least one radiation sensor for detection of the radiation scattered and/or transmitted from the body tissue, and/or an ECG unit for capturing an ECG signal via two or more ECG electrodes, and/or a temperature or heat sensor, and/or a bio-electrical impedance measuring unit.

25 Claims, 5 Drawing Sheets

(51) Int. Cl.
  *A61B 5/01* (2006.01)
  *A61B 5/02* (2006.01)
  *A61B 5/022* (2006.01)
  *A61B 5/024* (2006.01)
  *A61B 5/0402* (2006.01)
  *A61B 5/0404* (2006.01)
  *A61B 5/053* (2006.01)
  *A61B 5/145* (2006.01)

(52) U.S. Cl.
  CPC ...... *A61B 5/02416* (2013.01); *A61B 5/02438* (2013.01); *A61B 5/0402* (2013.01); *A61B 5/0404* (2013.01); *A61B 5/0537* (2013.01); *A61B 5/1455* (2013.01); *A61B 5/14532* (2013.01); *A61B 5/6887* (2013.01)

(58) Field of Classification Search
  USPC ....... 600/310, 316, 322, 323, 324, 331, 333, 600/335, 340, 344, 473, 476, 513
  See application file for complete search history.

(56) References Cited

U.S. PATENT DOCUMENTS

| | | | |
|---|---|---|---|
| 3,958,560 A * | 5/1976 | March | 600/319 |
| 4,610,254 A * | 9/1986 | Morgan et al. | 607/6 |
| 4,907,596 A | 3/1990 | Schmid | |
| 4,911,167 A | 3/1990 | Corenman et al. | |
| 4,928,014 A | 5/1990 | Rosenthal | |
| 4,934,382 A | 6/1990 | Barone, Jr. | |
| 4,938,218 A | 7/1990 | Goodman et al. | |
| 4,960,126 A | 10/1990 | Conlon et al. | |
| 5,153,426 A | 10/1992 | Konrad et al. | |
| 5,191,891 A | 3/1993 | Righter | |
| 5,237,178 A | 8/1993 | Rosenthal et al. | |
| 5,259,381 A * | 11/1993 | Cheung et al. | 600/323 |
| 5,309,916 A | 5/1994 | Hatschek | |
| 5,353,790 A | 10/1994 | Jacques et al. | |
| 5,431,170 A | 7/1995 | Mathews | |
| 5,515,847 A * | 5/1996 | Braig et al. | 600/316 |
| 5,676,143 A * | 10/1997 | Simonsen et al. | 600/316 |
| 5,682,902 A | 11/1997 | Herleikson | |
| 5,741,211 A * | 4/1998 | Renirie et al. | 600/300 |
| 5,771,891 A | 6/1998 | Gozani | |
| 5,795,305 A | 8/1998 | Cho et al. | |
| 5,924,996 A | 7/1999 | Cho et al. | |
| 6,041,247 A | 3/2000 | Weckstrom et al. | |
| 6,128,518 A | 10/2000 | Billings et al. | |
| 6,159,147 A * | 12/2000 | Lichter et al. | 600/300 |
| 6,190,325 B1 | 2/2001 | Narimatsu | |
| 6,230,035 B1 | 5/2001 | Aoyagi et al. | |
| 6,289,230 B1 | 9/2001 | Chaiken et al. | |
| 6,331,162 B1 | 12/2001 | Mitchell | |
| 6,714,814 B2 | 3/2004 | Yamada et al. | |
| 6,763,256 B2 * | 7/2004 | Kimball et al. | 600/336 |
| 6,790,178 B1 | 9/2004 | Mault et al. | |
| 6,819,950 B2 | 11/2004 | Mills | |
| 6,873,865 B2 * | 3/2005 | Steuer et al. | 600/322 |
| 7,215,991 B2 | 5/2007 | Besson et al. | |
| 8,046,059 B2 * | 10/2011 | Cho et al. | 600/513 |
| 2001/0012916 A1 | 8/2001 | Deuter | |
| 2002/0087087 A1 | 7/2002 | Oka et al. | |
| 2003/0009111 A1 | 1/2003 | Cory et al. | |
| 2003/0036685 A1 | 2/2003 | Goodman | |
| 2003/0055324 A1 * | 3/2003 | Wasserman | 600/323 |
| 2003/0109901 A1 | 6/2003 | Greatbatch | |
| 2004/0034293 A1 | 2/2004 | Kimball | |
| 2004/0116784 A1 | 6/2004 | Gavish | |
| 2004/0122336 A1 | 6/2004 | Jang et al. | |
| 2004/0152957 A1 | 8/2004 | Stivoric et al. | |
| 2004/0162493 A1 | 8/2004 | Mills | |
| 2004/0181132 A1 | 9/2004 | Rosenthal | |
| 2004/0225209 A1 | 11/2004 | Cho et al. | |
| 2004/0260165 A1 * | 12/2004 | Cho et al. | 600/326 |
| 2005/0013999 A1 | 1/2005 | Wakefield et al. | |
| 2005/0014999 A1 | 1/2005 | Rahe-Meyer | |
| 2005/0020936 A1 | 1/2005 | Lin | |
| 2005/0078533 A1 | 4/2005 | Vyshedskiy et al. | |
| 2005/0131282 A1 | 6/2005 | Brodnick et al. | |
| 2005/0177062 A1 | 8/2005 | Skrabal et al. | |
| 2005/0192488 A1 | 9/2005 | Bryenton et al. | |
| 2005/0261594 A1 | 11/2005 | Banet | |
| 2006/0009697 A1 | 1/2006 | Banet et al. | |
| 2006/0129040 A1 | 6/2006 | Fine et al. | |
| 2006/0135857 A1 | 6/2006 | Ho et al. | |
| 2006/0155193 A1 | 7/2006 | Leonardi et al. | |
| 2007/0038048 A1 * | 2/2007 | Gerder | 600/323 |
| 2007/0106139 A1 | 5/2007 | Nagata et al. | |
| 2007/0265533 A1 | 11/2007 | Tran | |
| 2008/0146892 A1 * | 6/2008 | LeBoeuf et al. | 600/300 |
| 2008/0200823 A1 | 8/2008 | Cho et al. | |
| 2008/0275317 A1 | 11/2008 | Cho et al. | |
| 2010/0004517 A1 | 1/2010 | Bryenton et al. | |
| 2012/0016210 A1 | 1/2012 | Kim et al. | |

FOREIGN PATENT DOCUMENTS

| | | |
|---|---|---|
| DE | 298 11 049 | 12/1998 |
| DE | 298 11 049 | 2/1999 |
| DE | 20 2005 001 894 | 5/2005 |
| EP | 1 317 902 | 6/2003 |
| EP | 1 407 713 | 4/2004 |
| EP | 1 491 134 | 12/2004 |
| WO | WO 90/04352 | 5/1990 |
| WO | WO 96/01585 | 1/1996 |
| WO | WO 99/62399 | 12/1999 |
| WO | WO 00/69328 | 11/2000 |
| WO | WO 01/65810 | 9/2001 |
| WO | WO 2005/048831 | 6/2005 |
| WO | WO 2005/077260 | 8/2005 |
| WO | WO 2006/099988 | 9/2006 |
| WO | WO 2007/017266 | 2/2007 |

OTHER PUBLICATIONS

Meir Nitzan, Boris Khanokh, "Infrared radiometry of thermally insulated skin for the assessment of skin blood flow," Optical Engineering 33, 1994, No. 9, pp. 2953-2956.

Cho et al., "Noninvasive Measurement of Glucose by Metabolic Heat Conformation Method," Clinical Chemistry, International Journal of Laboratory Medicine and Molecular Dianostics, 2004, vol. 50, No. 10, pp. 1894-1898.

Lepretre et al., "Effect of Exercise Intensity on Relationship between $VO_{2max}$, and Cardiac Output," Official Journal of the American College of Sports Medicine, 2004, pp. 1357-1363, XP-002428499.

Turner et al., "Effect of dried garlic powder tablets on postprandial increase in pulse wave velocity after a fatty meal: preliminary observations," Scandinavian Journal of Nutrition, 2005, vol. 49, pp. 21-26, XP-008079156.

European Search Report in EP 10 009 799.7, dated Nov. 11, 2010 with English translation of relevant parts.

Tao Dai et al., Blood Characterization From Pulsatile Biompedance Spectroscopy, CCECE 2006 (Canadian Conference on Electrical and Computer Engineering), pp. 983-986, Ottawa, Ontario.

* cited by examiner

MEDICAL MEASURING DEVICE

CROSS REFERENCE TO RELATED APPLICATIONS

This application is the National Stage of PCT/EP2007/010207 filed on Nov. 23, 2007, which claims priority under 35 U.S.C. §119 of German Application No. 10 2006 055 691.7 filed on Nov. 23, 2006, German Application No. 10 2007 042 551.3 filed on Sep. 7, 2007, and German Application No. 10 2007 042 550.5 filed on Sep. 7, 2007. The international application under PCT article 21(2) was not published in English.

The invention relates to a measuring device for non-invasive determination of at least one physiological parameter, comprised of at least one diagnostic sensor unit to generate measuring signals, and comprised of an evaluation unit for processing of measuring signals.

The supply of oxygen to the body tissue is known to belong to the most significant vital functions of a human being. For this reason, oximetric diagnosis modalities nowadays are of great importance in medicine. So-called pulsoximeters are utilized on a routine basis. The diagnostic sensor unit of such pulsoximeters typically comprises two light sources which irradiate red and/or infra-red light of a different wavelength into the body tissue. The light is scattered and partly absorbed in the body tissue. The scattered light is ultimately detected by means of a light sensor in form of a suitable photo cell (photo diode). Commercial pulsoximeters typically utilize light in a wavelength range of 660 nm. Light absorption of oxihaemoglobin and desoxihaemoglobin differs substantially within this range. The intensity of the light detected, scattered by the light sensor varies as a function of the intensity with which the examined body tissue is supplied with blood being rich and/or poor in oxygen. On the other hand, light in a wavelength range of 810 nm is typically applied. This light wavelength lies within the so-called near-infrared spectral range. Light absorption of oxihaemoglobin and desoxihaemoglobin within this spectral range is by and large identical. Moreover, prior art pulsoximeters are capable of generating a plethysmographical signal, i.e. a volume pulse signal which reflects the blood volume that is variable during a heartbeat in the microvessel system covered by the pulsoximeter (so-called photoplethysmography). If different light wavelengths are applied in the afore-mentioned spectral ranges, conclusions can be drawn from the different light absorption to the oxygen content in blood (oxygen saturation). Usual pulsoximeters are applied either at the finger tip or at the lobe of a patient's ear. Then the volume pulse signal is generated from the blood perfusion of the microvascular system in these areas of body tissue.

Known from WO 00/69328 A1 is an oximetric diagnosis device that can be utilized with special flexibility. This prior art device is manually operable so that it can be applied at arbitrary measuring points on a human body. The prior art device virtually allows for a systematic scanning of a patient's body. A fixation of the diagnosis device—as done with usual pulsoximeters—can be omitted with the device known from the afore-mentioned printed publication.

Moreover, the afore-mentioned WO 00/69328 A1 addresses the applicability of an oximetric diagnosis device for site-resolved recognition of inflammations, tumors, arteriosclerosis diseases in a patient's body tissue near the skin surface. Diseases of this type cause a change in blood circulation of body tissue. By way of the site-resolved oximetric scanning of a human body, changes in blood circulation suggesting a corresponding disease can be detected and localized with the afore-mentioned device.

The ECG (electrocardiogram) should be the most frequently applied examination modality for diagnosis of cardiovascular diseases. By means of the diagnostic sensor unit of an ECG device, electrical signals are derived with two or more ECG electrodes from the body of a patient to be examined. The ECG thus obtained reflects bioelectrical tensions that occur at a heart during ventricular stimulus conduction and repolarisation. The ECG contains numerous parameters that can be diagnostically evaluated. At the moment of contraction of a cardiac muscle during a heart beat, the ECG shows a clear peak which is also designated as R wave. Furthermore, the ECG contains the so-called P wave which precedes the R wave. The R wave is followed by the so-called T wave. The minimum levels in the ECG immediately before and immediately after the R wave are designated with Q and S, respectively. The parameters being of interest for cardiovascular diagnostics are the duration of the P wave as well as the amplitude of the P wave, the duration of the PQ interval, the duration of the QRS complex, the duration of the QT interval as well as the amplitude of the T wave. Conclusions to the health status of a cardiovascular system can be drawn from both the absolute values of the afore-mentioned parameters and from the ratios of these parameters. Devices and methods for ECG measurement are known, for example, from printed publications U.S. Pat. Nos. 6,331,162 or 4,960,126.

To determine other physiological parameters, e.g. body fat content, the principle of bioelectrical impedance measurement is known, for example, from U.S. Pat. No. 6,714,814. However, the composition of body tissue can also be determined optically. The principle of optical determination of body fat content by means of infrared light is described, for example, in U.S. Pat. No. 4,928,014.

It is the object of the present invention to provide a device for non-invasive determination of physiological parameters that is extended with regard to its functionality as compared with prior art in technology. More particularly, it is the object to create a device which can be utilized by a user in a comfortable and frequent manner in order to allow for a reliable and early recognition of diseases as well as for a continuous monitoring of existing diseases.

This task is solved by the present invention on the basis of a measuring device of the initially stated kind in such a manner that the diagnostic sensor unit is integrated into the keyboard of a computer or into a mobile device of entertainment or communication technology or is connectible to it, wherein the diagnostic sensor unit is comprised of an optical measuring unit comprised of at least one radiation source for irradiation of body tissue to be examined and at least one radiation sensor for detection of radiation scattered and/or transmitted by the body tissue, and/or comprised of an ECG unit for recording an ECG signal via two or more ECG electrodes, and/or comprised of a temperature or heat sensor.

By integrating the diagnostic sensor unit of the measuring device into the keyboard of a computer or into a mobile device of entertainment or communication technology, the user of a computer and/or mobile device can apply the measuring device at any time in order to determine those physiological parameters being of interest. Nowadays most persons have access to computers, be it in the office or at home. Moreover, most people utilize a mobile communication device, e.g. a mobile phone or a so-called smart phone. It is also common practice to utilize mobile entertainment devices, e.g. MP3 players or so-called walkmen. By integrating the diagnostic measuring unit into the keyboard of a computer or into a mobile device of entertainment or communication technology of the kind addressed hereinabove, it is ensured that the measuring device can be frequently applied by a user. A user can take a measurement to determine physiological parameters virtually simultaneously while working on a computer or using a corresponding device. Advantageously it is not necessary to use a separate device for this purpose. It is of particular advantage that the determination of physiological parameters can be done non-conspicuously, because from a third party's view the diagnostic measurement cannot be differentiated from a normal operation of the keyboard of a computer or a mobile device. For diabetics, in particular, the inventive measuring device lends itself suitable to determine the blood glucose level. Furthermore, the inventive measuring device is suitable to monitor and document the course of a therapy with an existing disease. A user can regularly apply the measuring device to record those parameters being of interest for the control of a therapy. These parameters can then be logged (including time and date of measurement), memorized or transmitted via a suitable data transmission net.

In accordance with the present invention, the diagnostic sensor unit can comprise an optical measuring unit to generate oximetric and/or plethysmographic measuring signals. It is thus made possible to monitor the supply of oxygen to the body tissue of the user and/or to generate a volume pulse signal.

The evaluation unit of the inventive measuring device is expediently equipped to determine at least one local metabolic parameter, the local oxygen consumption in particular, from the signals of the optical measuring unit. The evaluation unit utilizes the oximetric and/or plethysmographic measuring signals obtained by means of the optical measuring unit in order to not only determine the local oxygen concentration at given measuring site, i.e. in particular at the finger tips of the user of the keyboard or mobile device, but in particular the local oxygen consumption, too, as a significant indicator for local metabolic activity. By way of the inventive measuring device, diseases can be detected based on pathological changes in metabolism.

The optical measuring unit of the inventive measuring device comprises a radiation source for irradiation of the examined body tissue with electromagnetic radiation and at least one radiation sensor for detection of the radiation scattered and/or transmitted from the body tissue. Eligible for use as radiation source are conventional light-emitting diodes or even laser diodes which emit optical radiation, i.e. light within the corresponding spectral range. It has turned out to be particularly advantageous to measure the radiation absorption in the examined body tissue with the inventive device at least at two or—still better—three different optical wavelengths in order to determine the oxygen concentration of blood and the blood circulation of the tissue on this basis.

In accordance with a purposive configuration, the optical measuring unit of the inventive measuring device is comprised of at least two radiation sensors for detection of the radiation scattered and/or transmitted from the body tissue, with the radiation sensors being arranged at a different distance to the radiation source. This opens up the possibility of drawing conclusions on the distance covered by the radiation in the body tissue. On this basis, one can examine the oxygen concentration in blood and in differently deep tissue layers. One may utilize the circumstance that the measuring signals from tissue layers at a deeper level are more strongly influenced by arterial blood, while radiation absorption in those regions nearer to the surface is more strongly influenced by the blood in the capillary vessel system.

Of advantage is a configuration of the inventive measuring device in which at least two radiation sources are provided for which irradiate different volume ranges of the body tissue examined. Hereby, a differential measurement of light absorption can be simply realized. It makes it possible to examine metabolism-induced changes in blood circulation of the examined body tissue with blood being rich and/or poor in oxygen. The factor exploited here is that the local oxygen consumption changes as a function of the metabolic activity of the tissue. The determination of variable oxygen consumption in turn allows for drawing conclusions with regard to local energy consumption which is directly correlated with the oxygen consumption. Of particular interest is that this in turn allows for drawing conclusions on the glucose level. Thus the inventive measuring device advantageously allows for a non-invasive determination of the blood glucose level, too.

The two radiation sources of the optical measuring unit of the inventive measuring device should be so configured that volume ranges irradiated by them should be differently affected with regard to blood circulation with oxygen-rich or oxygen-starved blood. For example, this can be achieved in that the at least two radiation sources have different spatial radiation characteristics. For example, a light-emitting diode and a laser having similar wavelengths (e.g. 630 nm and 650 nm) can be utilized as radiation sources. The two radiation sources, however, differ by the angle of aperture of radiation. For example, whereas the light-emitting diode irradiates at a great angle of aperture into the examined body tissue, the light from the laser diode enters at a very small angle of aperture into the body tissue. As a consequence, different volume ranges of the body tissue are captured with the two radiation sources. On account of the large angle of aperture, a greater volume range of the epidermis not supplied with blood is captured by the light-emitting diode than by the laser. The epidermis not supplied with blood is practically not affected by a change in the haemoglobin concentration. Accordingly, the intensity of the light-emitting diode radiation scattered and/or transmitted from the body tissue is less strongly dependent on a change in haemoglobin concentration than the intensity of the radiation of the laser. The prerequisite is that the wavelength of the radiation emitted from both radiation sources each is so chosen that the radiation is absorbed in different intensity by oxihaemoglobin and/or deoxihaemoglobin. Therefore, the wavelength should range between 600 and 700 nm, preferably between 630 and 650 nm.

The evaluation unit of the inventive measuring device can advantageously be configured to determine a local metabolic parameter from the radiation of the two radiation sources scattered and/or transmitted from the body tissue. If oxygen is consumed in the examined body tissue, oxihaemoglobin is converted to deoxihaemoglobin. By a comparison of the radiation from the two radiation sources originating from the different volume ranges of body tissue, it is possible to determine the change in the concentration ratio of oxihaemoglobin and deoxihaemoglobin. This in turn results in the local oxygen consumption and ultimately (indirectly) into the blood glucose level. Thus, the evaluation unit of the inventive measuring device is expediently equipped to determine the local oxygen consumption and/or blood glucose level based on the intensities of the radiation from the two radiation sources scattered and/or transmitted from the body tissue.

With the inventive measuring device, the radiation sources and the radiation sensors are expediently arranged at the user interface of the keyboard, for example at some lateral space to the operating keys of the keyboard. With this configuration, the optical measuring unit of the measuring device can be utilized at any time while working on a computer, for example by laying a finger onto a measuring field at the user interface of the keyboard in which the radiation sources and the radiation sensors are arranged. Alternatively, the radiation sources and radiation sensors can be arranged at the outside of the casing of the relevant mobile entertainment or communication device in order to allow for utilizing the measuring device at any time. The radiation sources and sensors need not be arranged directly at the surface. Alternatively, the radiation can be transmitted via optical fibres that are laid from the surface of the keyboard and/or device casing to the radiation sources and/or sensors arranged in the interior.

In accordance with a preferred embodiment, the inventive measuring device additionally comprises a measuring unit integrated into the keyboard and/or mobile device of entertainment or communication electronics to record local tissue parameters, such as fat content, water content and/or blood circulation, wherein the evaluation unit is properly equipped to determine at least one local metabolic parameter from the signals of the optical measuring unit and tissue parameters.

For example, a significant local tissue parameter in the sense of the present invention is blood circulation. Meant thereby are the volumetric fluctuations of the examined body tissue caused by blood circulation. To record blood circulation, the inventive measuring device can be equipped with a conventional plethysomgraphical unit o(e.g. a photoplethysmograph), as has already been outlined hereinabove. Thus the optical measuring unit of the inventive measuring device can be utilized at the same time to record local tissue parameters.

The present invention is based on the finding, among others, that a combination recording oximetric and plethysographic signals opens up the possibility to determine local metabolic parameters.

To determine the local oxygen consumption, it should also be possible by means of the inventive measuring device to determine the capillary oxygen concentration in tissue in addition to the oximetrically determined arterial oxygen concentration. But this requires knowing the composition of the examined body tissue. The crucial parameters are local fat content and/or water content of body tissue. For example, these parameters can be recorded by means of a bio-electrical impedance measurement. In accordance with an expedient embodiment of the present invention, a conventional (optical) oximetry unit is therefore combined with a bio-electrical impedance measuring unit in a unique device. From the measuring signals obtained by means of the bio-electrical impedance measuring unit, for example, the composition of the body tissue examined can be determined. On this basis, it is then feasible to determine the capillary oxygen saturation in the tissue from the oximetric signals by means of the evaluation unit of the measuring device, For the bio-electrical impedance measurement, electrodes are expediently integrated into the user interface of the keyboard and/or into the casing surface of the device of entertainment or communication technology. It makes specific sense, if one electrode feeding an electric current and one measuring electrode each are so arranged at the outsides of the casing, for example of a mobile phone, that the user of the device can touch one electrode with one hand and the other electrode with the other hand. Other possibly existing sensors of the inventive measuring device should also be arranged in the area of the measuring electrodes, so that the user can hold the device tight with both hands while all the required measurements are taken simultaneously. Then the measuring results can be indicated on the integrated display of the device in a well legible manner for the user.

For conventional measuring methods to determine the bioelectrical impedance, a measurement is taken for example between one hand and one foot of the person to be examined, and thereof it results a global index for each side of the body measured. The diagnostic sensor unit of the inventive measuring device may be comprised of a bio-electrical impedance measuring unit, comprising one pair of feeder electrodes to supply electrical alternating current and one pair of measuring electrodes for impedance measurement. The distance between the pair of feeder electrodes and the pair of measuring electrodes expediently accounts for less than 10 cm, preferably for less than 1 cm. By shortening the electrode distance to less than a few millimeters up to a few centimeters, integration is not done across the entire body according to the present invention, but the bio-electrical impedance is recorded locally. Thereby it is possible to determine local changes in impedance. For example, the local bio-impedance changes due to the changing blood volume within a pulsation. Thereby it is possible to determine the heart frequency via the local bio-electrical impedance. The pulse amplitude is simultaneously determined as a significant physiological parameter. It has become evident that this pulse amplitude correlates with the body temperature, which means that it is possible to determine the temperature of the examined body spot by the aid of a bio-impedance analysis. Furthermore, the local bio-impedance depends on the volume of liquid, i.e. on the local blood volume in the examined tissue, whereby it is possible to determine the local blood circulation of the examined tissue. Finally, the local bio-electrical impedance of the body changes as a function of food intake, so that metabolism which exerts a decisive influence on the blood glucose level can be examined by means of bio-impedance. The inventive measuring device, therefore, also allows for an indirect non-invasive monitoring of the blood glucose in which the effect of glucose and/or the energy demand of the physiological reaction in the body initiated by glucose is examined. To this effect, various physiological parameters, e.g. cardiac activity and/or blood circulation and/or body temperature and/or bio-impedance are utilized to describe metabolism. By applying a suitable algorithm, it is possible to determine the blood glucose level from recorded measuring signals of the bio-electrical impedance analysis, possibly in combination with the measuring signals of other measuring modalities of the inventive device.

A purposive development of the inventive measuring device provides for configuring the bio-electrical impedance measuring unit moreover to record global tissue parameters such as global fat content and/or global water content. The functionality of the inventive measuring device is hereby extended. The bio-electrical impedance measuring unit of the inventive measuring device can be so configured that both local and global tissue parameters can be measured thereby.

The composition of body tissue can also be determined optically with the inventive measuring device. The principle of optical determination of body fat content by means of infrared light is known from prior art in technology. The optical measuring unit of the inventive measuring device can be utilized to this effect In accordance with an advantageous configuration, the inventive device comprises an integrated temperature and heat sensor. This can be utilized to determine local heat production. In the simplest case, the temperature sensor is properly configured to measure the surface temperature of the skin at the measuring point. Preferably a heat measurement resolved for place, time and depth at the measuring point is rendered feasible by means of the heat sensor. Based on the heat exchange, conclusions can be drawn as to the local metabolism activity. Moreover, the heat sensor is suitable for determining local blood circulation. Concerning more precise background information on heat measurement, reference is made to the publication made by Nitzan et al. (Meir Nitzan, Boris Khanokh, "Infrared Radiometry of Thermally Insulated Skin for the Assessment of Skin Blood Flow", Optical Engineering 33, 1994, No. 9, P. 2953 to 2956). On the whole, the heat sensor supplies data which can advantageously be utilized for the determination of metabolic parameters.

The arterial oxygen saturation ($SaO_2$) and the venous oxygen saturation ($SvO_2$) depending on the type of tissue examined determine the capillary (arteriovenous) oxygen saturation ($StO_2$). Applicable is:

$$K*SvO_2+(1-K)*SaO_2=StO_2$$

wherein K is a tissue-dependent corrective factor which depends on the volumetric ratio between arteries and veins in the examined tissue. On average, this value lies slightly under 0.5. In accordance with the invention, the value decisive for the relevant tissue can be determined by bio-electrical impedance measurement in order to then determine the venous oxygen saturation based on the a.m. formula. By means of the temperature and/or heat measurement and/or bio-electrical impedance (impedance plethysmography) it is possible to determine blood circulation V, i.e. the volume fluctuation of the body tissue examined which is conditioned by blood circulation. According to the relation $$VO_2=V*(SaO_2-SvO_2)$$

one can finally compute the local oxygen consumption $VO_2$ which is a measure for the metabolic activity at the measuring point.

By way of an ECG unit to record an ECG signal via two or more electrodes, the functional scope of the inventive measuring device is advantageously extended. In accordance with this advantageous development of the present invention, plethysmographic signal and ECG signals in combination are recorded and evaluated by means of the measuring device. The evaluation unit of the measuring device can then be advantageously equipped for evaluating the chronological course of the volume pulse signals and ECG signals. By means of a suitable program control, the evaluation unit of the inventive measuring device is capable of recognizing the R waves in the ECG signal automatically. The exact point of time of a heartbeat is thus automatically determined. On account of its program control, the evaluation unit furthermore is capable of recognizing the maximum levels in the volume pulse signal. Based on the maximum levels in the volume pulse signal, the point of time of the arrival of a pulse wave triggered during a heartbeat can be detected and realized at the peripheral measuring site captured by the measuring device. Finally, it is thus possible to determine the chronological interval between an R wave in the ECG signal and the succeeding maximum in the volume pulse signal. This chronological interval is a measure for the so-called pulse wave velocity. On the one hand, based on the pulse wave velocity, one can make a statement on the blood pressure. A shortening in the pulse wave velocity is accompanied by an increase in blood pressure, while an extension in the pulse wave velocity suggests a decrease in blood pressure. However, it is not possible to exactly determine the blood pressure from the pulse wave velocity as only tendencies can be indicated. Furthermore the pulse wave velocity depends on the density of blood and in particular on the elasticity of blood vessel walls (for example of the aorta). From the elasticity of blood vessels, in turn, one can draw a conclusion as to a possibly existing arteriosclerosis. The absolute values of heart frequency, heart frequency variability and corresponding arrhythmia of the heart can also be considered in this evaluation. For example, arrhythmia like Sinus Tachycardia, Sinus Bradycardia, Sinus Arrest and so-called Escape Beats can be determined automatically. Based on the ECG signal, it is also possible to make statements on the temporal duration of the auricular systole of the heart with one heartbeat, on the temporal duration of the heart chamber contraction as well as on the duration of the relaxation of the heart chamber etc. Moreover, preliminary diagnoses relating to so-called blocks in the duct of electrical exciter signals at the heart (AV block, bundle branch block, etc.) and even with regard to disturbances in blood circulation or infarcts are rendered possible. Other irregularities in the pulse course can be detected on the basis of the volume pulse signal.

By combining the evaluation of the ECG signal with the volume pulse signal in the automatic evaluation, the inventive measuring device is autonomously able to render a functional evaluation of a patient's vascular system. On the basis of the automatically evaluated signals, the inventive device can roughly estimate the (global) cardiovascular status or, in general, the user's fitness and if there is any indicative evidence of an arteriosclerosis or other cardiovascular problems it can generate a corresponding warning signal or an easy to interpret fitness or risk indicator for the user of the device and display it, for example via a monitor connected to a computer which the keyboard is linked to or via an integrated display of the mobile device of the entertainment or communication technology. Thus the inventive measuring device can advantageously be utilized for auto-diagnosis of cardiovascular diseases.

Of particular advantage is the inventive combination of the afore-mentioned measuring methods, i.e. the oximetry, ECG measurement, temperature and/or heat measurement and bio-electrical impedance measurement. By means of the evaluation unit of the device, all measuring signals can be evaluated by a suitable algorithm and be combined in order to examine the metabolism. By a combination of the various measuring modalities, a high efficiency and reliability in the recognition of pathological changes is achieved. All parameters can advantageously be summarized to a global index which is easy to interpret for a user and which gives a user a direct and substantiated hint as to its general health status.

The combination of various measuring modalities summarized in the inventive measuring device as outlined hereinabove is furthermore advantageous because a non-invasive indirect measurement of the glucose concentration becomes feasible thereby. A possible approach in the determination of the blood glucose level by means of the inventive device is explained and outlined in greater detail as set forth below:

The inventive measuring device serves for measurement and evaluation of data influenced by metabolism. It is self-evident that the energy budget and composition of food taken-in by a user of the measuring device play an important role. Nutrients involved in metabolism mainly are carbon hydrates, fats and proteins, as is well known. For further processing, carbon hydrates are converted into glucose, proteins are converted into amino acids, and fats are converted into fatty acids. The energy carriers are then converted in the cells of body tissue together with oxygen by dissipation of energy to ATP (adenosintriphosphoric acid). ATP is the actual endogenous energy carrier. Preference is given to the use of glucose to generate ATP. But if the production of ATP from glucose is impeded (e.g. due a lack of insulin), an intensified fatty acid oxidation occurs instead. However, the oxygen consumption in this process is different.

The reaction of the metabolism of the human body to a take-up of food characteristically depends on the composition of the food, as has been outlined above. For example, the vascular system of the body reacts depending on how much energy is needed by the body to digest the food taken-up. Based on the pulse wave velocity which can be determined by means of the inventive measuring device as well as based on the blood pressure amplitude and based upon the pulse, the reaction of the body to the take-up of food can be determined. To this effect, the evaluation unit of the inventive measuring unit is properly equipped to evaluate the temporal course of pulse wave velocity and to determine the composition of the food taken-up by a user of the measuring device based on the temporal course of the pulse wave velocity from the moment of food take-up. The pulse wave velocity as well as the blood pressure amplitude and the pulse change as soon as the food take-up commences. The maximum levels and the relevant points of time of these maximum levels are influenced by the composition of food. The course and the absolute level of pulse wave velocity, blood pressure amplitude and pulse can be taken recourse to in order to determine the composition of the food taken-up by means of the evaluation unit of the inventive measuring device.

In its normal status, i.e. in dormancy and in the so-called thermoneutral zone, the metabolism of a human body is mainly determined by the glucose balance. Therefore, the glucose concentration in the cells of body tissue in this normal status can be described as a mere function of heat production and oxygen consumption. Applicable is:

$$[Glu]=f_1(\Delta T, VO_2),$$

with [Glu] representing the glucose concentration. The heat production $\Delta T$ can be determined ($\Delta T=T_\infty-T_{artery}$) by means of the heat sensor of the inventive measuring device, e.g. from the difference between the arterial temperature and the temperature which the skin surface would reach with a perfect thermal insulation. The term $f_1(\Delta T, VO_2)$ indicates the functional dependency of the glucose concentration on heat production and on oxygen consumption. The oxygen consumption is obtained, as outlined hereinabove, from the difference between venous and arterial oxygen saturation and blood circulation. To determine the glucose concentration during and/or directly after food intake, however, a corrective term must be considered which reflects the portion of lipometabolism in the energy balance. Then the following is applicable:

$$[Glu]=f_1(\Delta T, VO_2)+X*f_2(\Delta T, VO_2).$$

X is a factor which is negative after food intake. Accordingly, X depends on the composition of the food taken in. In particular, X depends on the ratio in which fat and carbon hydrates participate in the metabolism. As outlined above, the factor X can be determined based on the temporal course of the pulse wave velocity. X is zero, if mere carbon hydrates or directly glucose are taken-up. The amount of X rises, the greater the portion of fat in the food taken in. To determine the corrective factor X from the temporal course of the pulse wave velocity, blood pressure amplitude and/or pulse, a calibration of the inventive measuring device is usually required for adaptation to the relevant user of the device.

For fat metabolism, $f_2(\Delta T, VO_2)$ indicates the functional dependency of the glucose concentration on the heat production and on the oxygen consumption.

Thus the evaluation unit of the inventive measuring device can be utilized to determine local glucose concentration from local oxygen consumption and local heat production. The measuring device must comprise the appropriate measuring modalities to this effect. As outlined hereinabove, the determination of oxygen consumption can be performed by combining oximetry with bio-electrical impedance measurement. An additional suitable heat sensor is then still required to determine heat production. Finally, in order to be able to compute the glucose concentration in accordance with the a.m. functional correlation, the corrective factor X should be determined, for example from the temporal course of the pulse wave velocity. As has also been outlined hereinabove, this can be accomplished by a combined measurement of ECG signals and plethysmographical signals. Hence, to determine the glucose concentration, a pulsoximeter, an ECG unit, a bio-electrical impedance measurement as well as a heat sensor are expediently combined in the inventive measuring device.

The method outlined hereinabove initially just allows for a determination of the intracellular glucose concentration. In a simplified approach, there is the following correlation with blood glucose concentration:

$$[Glu]_{cell}=a+b*\ln(c*[Glu]_{blood})$$

The constants a, b, and c depend on the individual physiology of the user of the measuring device. The evaluation unit of the inventive measuring device can furthermore be configured to determine the blood glucose level from local glucose concentration, with it being necessary to consider parameters that depend on the physiology of the user of the measuring device. These parameters can be determined by an appropriate calibration, for example by a comparison with blood glucose values invasively determined in a conventional manner.

For realization of the inventive measuring device in practice, the computer which the keyboard is connected to advantageously forms the evaluation unit; the functions of the evaluation unit described before are realized by a software running on the computer and the physiological parameters determined by means of the software are memorized and saved by means of the computer. With this configuration, the data processing electronics which is in any way existing with a computer is utilized for processing the measuring signals obtained by means of the diagnostic measuring unit. This is easy to accomplish by providing appropriate software. At the same time, the physiological parameters determined by means of the software can be memorized and saved by the computer. This makes it possible to follow-up and document the course of a disease and the effects of a corresponding therapy.

Alternatively, a microprocessor or microcontroller which is in any way existing in the appliance of entertainment or communication technology serves as evaluation unit, with the functions of the evaluation unit being realized by a software running on the microprocessor or microcontroller.

It is furthermore purposive for the inventive device to comprise a diagnostic unit to evaluate the physiological parameters determined by means of the evaluation unit. The functions of the diagnostic unit in turn can be realized by software. The evaluation unit is in charge of evaluating recorded signals in order to determine the parameters required for diagnostics in the manner as described hereinabove. These parameters are then further processed by the diagnostic unit in order to draw conclusions relative to diseases, if any. The diagnostic unit is also in charge of automatically recognizing the existence of a disease, particularly if the measuring device is utilized by a user for auto-diagnosis, and to generate an appropriate warning signal for the user.

Hence, the diagnostic unit of the inventive measuring device is expediently equipped to determine the status of the cardiovascular system from the parameters determined by means of the evaluation unit. In accordance with a particularly advantageous configuration of the present invention, the diagnostic unit is furthermore properly equipped to compute a global fitness index on the basis of the status of the cardiovascular system and the global tissue parameters (recorded by means of bio-electrical impedance measurement). Thus the global tissue parameters can be utilized to obtain the global fitness index which is particularly informative on the momentary health status of a user. To determine the global fitness index all recorded measuring values of a user can be considered. If required, an average value is determined over a definable period of time. Apart from the cardiovascular measuring values and the global tissue parameters (global fat content, global water content), the local tissue parameters as well as the local metabolic parameters (e.g. local oxygen consumption) can also be considered. The result of the global fitness index is a single value which is particularly easy to interpret by the user of the measuring device.

A display unit, for example a conventional monitor, is expediently linked to the computer of the inventive measuring device to indicate the determined physiological parameters and to issue the examination findings and results generated by the diagnostic unit. Alternatively, a display which is anyhow existing with an appliance of entertainment and communication technology is suitable to serve as a display.

Expediently the inventive measuring device is properly equipped for remote data transmission, that means for transmission of medical measuring signals or determined physiological parameters via a data or communication net. For example, the data transfer can be realized by means of a computer which the keyboard including the measuring unit are connected to in accordance with the present invention, through a data network (e.g. internet). As an alternative, the physiological parameters can be transmitted via a mobile radio network if the measuring device according to the present invention is integrated into a mobile phone, for example. The measuring signals or the physiological data, for example, can be transmitted to a central station (healthcare center) for a more thorough analysis and documentation as well as for monitoring the chronological development of individual parameters. There, the data are evaluated for example by means of suitable analysis algorithms, considering filed patient data (including information on chronic diseases or previous diseases). The result in turn can be sent back via the relevant data or communication net to the measuring device in order to inform the user of the device about its health status. From the central station, further selective measurements, if required, can be initiated by the inventive measuring device. Moreover, for the purpose of an extended anamnesis caused by the evaluation results, back-queries can be transmitted back to the patient via the data and communication network. The data and evaluation results can automatically be transmitted to the examining physician. If hints to a medical case of emergency become evident from the measuring and evaluation results, the required measures (e.g. automatic alarming of the rescue service) can be initiated immediately. Another advantage of remote data transfer lies in that the required software for evaluation of measured signals need not be implemented in the device itself, but merely at a central location where the data are received, and must be kept available and maintained in proper status.

A particularly practical configuration of the inventive measuring device is obtained, if the computer is a mobile appliance, more particularly a notebook, laptop, palmtop or handheld. In this case, the diagnostic measurements can be taken by the use of the computer at any time, even if being under way.

For photoplethysmographical measurements, the contact pressure of a finger on the optical sensor has a significant influence on the measuring signals. Accordingly, it may make sense to equip the inventive measuring device with means to determine the contact pressure of a finger laid on the measuring unit. This may be a conventional pressure sensor, for example in form of a piezoresistive element. Optical processes to determine the finger contact pressure are also feasible. It is also conceivable to determine the finger contact pressure from the (photoplethysmographic) signals themselves, because the finger contact pressure takes a characteristic influence on the measuring signals. The determined finger contact pressure can then be considered in the further evaluation of the measuring signals in order to compensate for the influence of the contact pressure on blood circulation, for example.

A purposive development of the inventive measuring device results from integrating an additional temperature sensor to determine the ambient temperature in the environment of the measuring device. For example, the use of a temperature sensor whose function is based on the measurement of the sound spread velocity in ambient air lends itself suitable. Ambient temperature influences the metabolism of a human body. To this extent it makes sense to consider the ambient temperature in the evaluation of the measuring signals obtained by means of the measuring device.

In accordance with an advantageous configuration of the present invention, the measuring device comprises one or several temperature sensors to determine the body core temperature. Expediently the temperature sensors are arranged in a position in which they can be directly brought in contact with the body spots to be examined. Alternatively, the temperature sensor for determination of the body core temperature may be a unit separated from the computer keyboard or from the mobile appliance which is linked via a wireless (e.g. Bluetooth) or wired link to the keyboard and/or to the mobile appliance. In this manner, the unit for measuring the body core temperature can be handled without any problems to measure the temperature. A conventional sensoric system of an actually known kind can be utilized to measure the body core temperature. The body core temperature represents a significant reference variable, which can be considered in the determination of physiological and particularly metabolic parameters in the sense of the present invention.

Thus the evaluation unit of the inventive measuring device can advantageously be properly equipped to determine the breathing frequency from the measuring signals of the measuring device. For example, the breathing frequency can be estimated based on the photoplethysmographically determined pulse amplitude. The pulse amplitude in turn reciprocally depends on the heart frequency.

In accordance with a preferred embodiment of the present invention, it is provided for that the at least one diagnostic sensor unit forms a unit separated from the mobile device of entertainment and communication technology and connected to the mobile device via a cordless or cord-bound signal line. It means that the functionality of the measuring device is integrated into the mobile device. But the sensorics itself is separated from the mobile device. This configuration is particularly suitable for a continuous monitoring of the blood glucose value or other physiological parameters, because the measuring unit can be permanently arranged at a suitable spot of the user's body, for example independently from the mobile device. The evaluation unit may be located either in the measuring unit, too, or in the mobile device which the measuring unit is connected to.

In its functionality, the inventive measuring device can still be extended in that the diagnostic sensor unit comprises a unit for the analysis of samples, like blood, urine, stools, breathing air, sweat, saliva, hair, hormone samples or the like. Thus the device also fulfils the function of a private medical laboratory that is easy to use by the user of the device. This function is purposive both for continuous monitoring and applications in case of emergency.

In accordance with a purposive development of the present invention, the optical measuring unit and the temperature or heat sensor are arranged in a common sensor casing, with a planar ECG electrode being configured at the upper side of the sensor casing having at least one recess to allow for the passage of the radiation emitted from the at least one radiation source. The planar ECG electrode expediently comprises another recess for the temperature or heat sensor. The radiation source, radiation sensor and the temperature or heat sensor can be arranged on a common printed circuit board within the sensor casing. Thus the required measuring modalities are summarized in the sensor casing which forms a unit that can be integrated into a computer keyboard or into a mobile device flexibly and without any problem. It is also conceivable to configure the sensor casing in a detachable and connectible arrangement with a keyboard or a mobile device (e.g. via a suitable plug connection) so that the measuring sensorics is available only on demand. Moreover, this configuration allows for a retrofitting the keyboard or mobile device with the inventive measuring functionality. The sensor casing should have dimensions being less than 1 cm×1 cm×1 cm in order to be utilized unproblematically and flexibly in the sense of the present invention. At the upper side of the sensor casing, at least one additional planar electrode can be configured which serves as feeder or measuring electrode of the impedance measuring unit in order to additionally allow for taking a bio-electrical impedance measurement.

In accordance with a purposive development of the present invention, the measuring device additionally comprises a blood pressure measuring unit to measure the systolic and/or diastolic blood pressure. Blood pressure represents a significant reference variable, which can be additionally considered in the determination of physiological and metabolic parameters in the sense of the present invention in order to improve the reliability of findings and results. The blood pressure measuring unit may be a sphygmomanometer of the conventional type with an associated sensoric system as applied already nowadays with commercial-type blood pressure measuring instruments, for example with electronic blood pressure measuring instruments utilized on the wrist. The blood pressure measuring unit can be connected in a wire-bound or wireless manner to the computer keyboard and/or to the mobile device in accordance with the present invention.

Practical examples of the invention are elucidated more precisely in the following by taking reference to the drawings, wherein.

Figure 1:
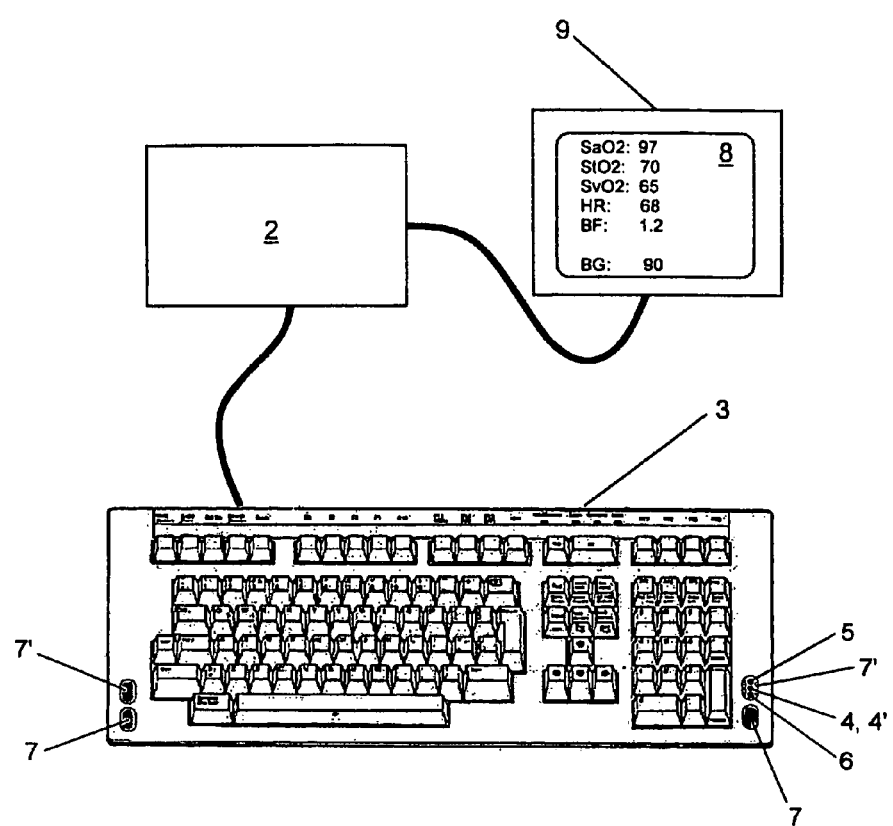
FIG. 1 shows a schematic view of a first embodiment example of the inventive measuring device.

FIG. 1 shows a first embodiment example of the inventive measuring device. The measuring device is comprised of a computer 2 which is connected to a keyboard 3. Various medical measuring modalities are integrated into the user interface of the keyboard 3. This is touched by a user of the device with the finger tips to execute a measurement. Integrated into the keyboard are light sources 4, 4', for example in form of light-emitting diodes that are capable of emitting light at various wavelengths. For this purpose, various light-emitting semiconductor elements, for example, are accommodated in a common casing. It is also conceivable to use optical waveguides to guide the light from various light sources to the user interface of keyboard 3. Furthermore, the keyboard 3 is comprised of one or several photo sensors 5. These photo sensors are arranged in immediate vicinity to the light source 4 and 4', respectively. Sensors 5 receive the light from light source 4 and/or 4' scattered in the tissue at the user's finger tip. Moreover, a heat sensor 6 is provided immediately next to light source 4 and/or 4'. Hereby it is ensured that the determination of blood supply based on heat measurement is accomplished at the same measuring place as the optical measurement. Besides, a total of four electrodes 7 and/or 7' are provided at the user interface of keyboard 3 to measure the local bio-electrical impedance. The device user touches two electrodes 7 and/or 7' each simultaneously with one hand. One of the two contact surfaces serves to impress an electrical current at the measuring place, while the other contact surface is utilized for voltage measurement. In this manner it is ensured that the measuring results are not influenced by the contact resistance of the measuring electrodes. The two electrodes designated by reference number 7 are also utilized as ECG electrodes of an ECG of the measuring device which is also integrated into the keyboard 3. The two electrodes each are touched with the finger tips so that a two-point derivation (arm-to-arm measurement) is obtained. The measuring signals picked-up by the sensors integrated into keyboard 3 are processed by means of computer 2. Physiological parameters thus obtained are then displayed on a display screen 8 of a monitor 9 connected to computer 2. For example, the display shows the arterial ($SaO_2$), capillary ($StO_2$) and venous ($SvO_2$) oxygen saturation. Furthermore displayed is the determined heat frequency (HR) and fat content of tissue (BF). Finally, a blood glucose value (BG) is also indicated. The user can determine the physiological parameters being its interest at any time. For this purpose, a user merely lays the fingers with which a user would actuate the keys of keyboard 3 onto electrodes 7, 7'. The parameters are then displayed immediately by means of monitor 9 after processing of measuring signals by means of computer 2. A user of device 1 practically does not have to interrupt its work on computer 2 to determine the physiological parameters.

With the practical example illustrated in FIG. 1, two radiation sources 4 and 4' are provided for which irradiate different volume ranges of the body tissue examined. To this effect, the two radiation sources 4 and 4' have different spatial radiation characteristics, namely different radiation angles. Radiation source 4 is a light-emitting diode, while radiation source 4' is a laser, for example a so-called VCSEL-laser (vertical cavity surface emitting laser). Both light-emitting diode 4 and laser 4' emit light with a very similar wavelength (e.g. 630 nm and 650 nm), but with different aperture angles (e.g. 25° and 55°). With the arrangement shown in FIG. 1—as described hereinabove—it is possible to take a differential measurement of metabolism-induced alterations in the oxygen content in blood. To this effect, the wavelength of the radiation emitted from both radiation sources 4 and 4' each must be within a range in which the light is absorbed in different intensity by oxihaemoglobin and deoxihaemoglobin. To allow for taking an absolute measurement of the oxygen content in blood (oxygen saturation), there must be further radiation sources (not shown in FIG. 1), the optical wavelength of which lies in a spectral range in which light absorption by oxihaemoglobin and deoxihaemoglobin is mainly identical (so-called isobectic point). The light emitted from the light-emitting diode and/or the laser can be conducted by means of appropriate optical fibres to the relevant spot at the user interface of the keyboard. In this case, the relevant fibre ends are designated with reference number 4 and 4' in FIG. 1. It is feasible to link the light-emitting diode and the laser to the appropriate fibres in such a manner that they radiate with the desired different angle of aperture into the body tissue to be examined. Accordingly, different volumes of the body tissue are examined with both radiation sources. On account of the greater angle of aperture, the portion of the epidermis not supplied with blood at the body tissue examined by means of the light-emitting diode is greater than it is with a laser. The light both from radiation source 4 and radiation source 4' scattered in the body tissue and partly absorbed is detected by means of sensors 5. Sensors 5 need not be arranged directly at the user interface of keyboard 3. Instead, the light can be supplied via the light-conducting fibres to the sensors arranged in the interior of keyboard 3. To differentiate the light of radiation source 4 from the light of radiation source 4', both light sources 4 and 4' can be operated in different time modules, with the signals detected by sensors 5 being accordingly demodulated. Alternatively it is possible to differentiate the radiation from both radiation sources 4 and 4' based on the different wavelength. The radiation intensity of the radiation emitted from radiation sources 4 and 4' is attenuated with the path length on passage through the body tissue, with the correlation of intensity attenuation to the concentration of the absorbing substance (oxygenated haemoglobin) being given by the well-known Lambert Beer law. By means of the sensors 5 illustrated in FIG. 1, the interesting parameters of intensity attenuation can be determined, that means separately for the volume ranges of the examined body tissue captured by radiation sources 4 and 4' each. The parameters of intensity attenuation to be allocated to the different radiation sources 4 and 4' can be related to each other by means of the evaluation unit of the inventive measuring device in order to take a differential measurement in this manner. In the simplest case, quotients are computed from the parameters of intensity attenuation of the radiation from both radiation sources 4 and 4'. From alterations in these quotients, conclusions can be drawn with regard to alterations in the metabolism. For example, if the blood glucose level rises after food intake, accordingly more glucose will enter into the cells of body tissue (after a certain temporal retardation) and transformed there. Oxygen is consumed in this process. This oxygen is received by the cells through blood. Accordingly, by the dissipation of oxygen, oxigenated haemoglobin becomes deoxigenated haemoglobin. The ratio of deoxigenated haemoglobin versus oxigenated haemoglobin rises accordingly. On account of the different angles of aperture of the radiation from radiation sources 4 and 4', alterations in the haemoglobin concentration take a different impact on the relevant intensity attenuation. Thus, alteration in the haemoglobin concentration can be detected from the quotients of the parameters of intensity attenuation. This makes it possible to draw an indirect conclusion as to oxygen consumption. Since oxygen consumption depends on the blood glucose level, it is also possible to determine the blood glucose level by means of the differential measurement of radiation absorption as outlined hereinabove. To supplement this process, a bio-impedance analysis is performed in parallel to the optical measurement, with the electrodes 7 and 7' shown in FIG. 1 being provided for this purpose. The purpose of a bio-impedance measurement above all is to determine local supply with blood. It can serve as another parameter to determine oxygen consumption and blood glucose level, too. Different angles of aperture of the radiation can also be generated with one radiation source 4 only by utilizing appropriate optical elements (e.g. beam divider, lenses, etc.).

Figure 2:
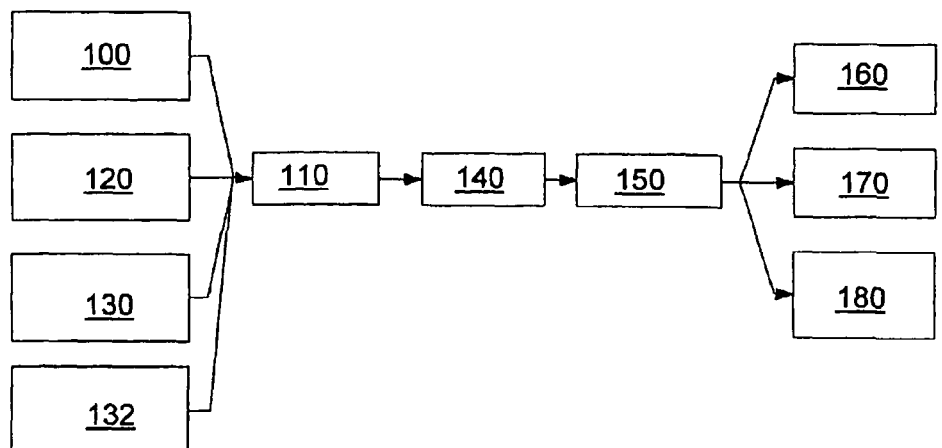
FIG. 2 shows the inventive device based on a block diagram.
Figure 3:
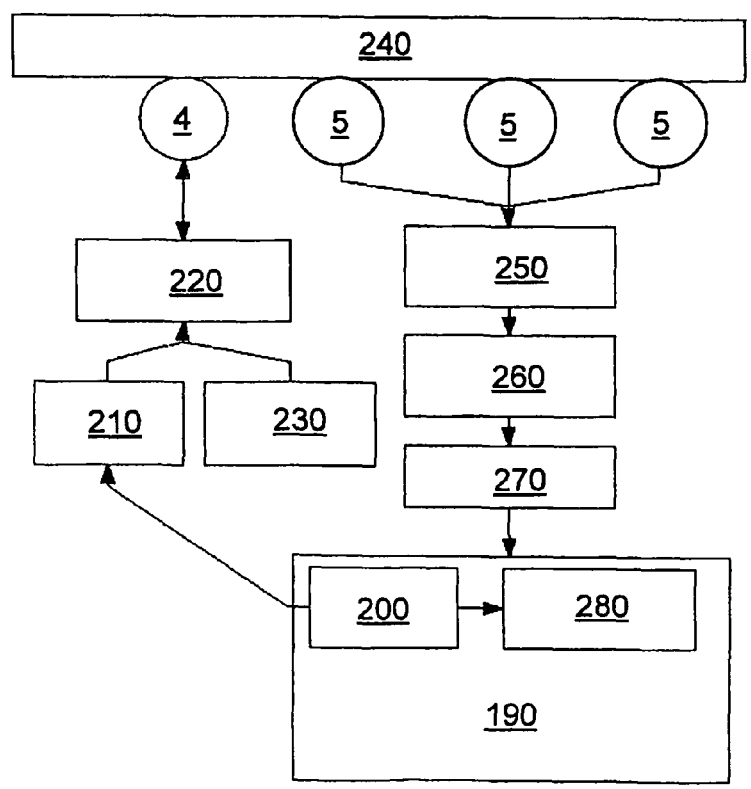
FIG. 3 shows a block diagram of the oximetry unit of the inventive measuring device.

FIG. 2 schematically shows the set-up of the inventive measuring device as a block diagram. The device 1 is comprised of an optical measuring unit 100 for optical measurement of the oxygen concentration in the blood vessel system of the body tissue at a given measuring spot. The oximetric and plethysmographic signals recorded by the optical measuring unit 100 are passed on to an analyser unit 110. Another essential component of device 1 is a heat measuring unit 120 to determine local heat production. The heat measuring unit 120 is a special heat sensor which isolates the examined body spot. This spot thus can take-up or discharge heat only through the stream of blood. Therefore it is possible to determine the supply with blood and the heat production by a time-resolved measurement of the temperature. With a strong supply with blood, the examined body spot reaches its maximum temperature within a very short period of time. With a small supply with blood, it takes longer time. In addition, via the extrapolation of the measured temperature, one can draw a conclusion as to the arterial temperature, because the temperature at the place of measurement is only determined by the arterial temperature and by local heat production. Even the measuring signals recorded by means of the heat measuring unit 120 are passed on to the analyzer unit 110 for further processing. Besides, the device is comprised of an impedance measuring unit 130 which serves to record local tissue parameters by means of bio-electrical impedance measurement. The measuring signals of the impedance measuring unit 130 are also processed by means of the analyzer unit 110. Finally, in accordance with the present invention, an ECG unit 132 is also provided for to record an ECG signal. The ECG unit 132, too, is linked to the analyzer unit 110 to process the ECG signals. Allocated to the optical measuring unit 100 are the light source 4 as well as the light sensors 5 of the keyboard 3 illustrated in FIG. 1. The heat measuring unit 120 is connected to the heat sensor 6. The impedance measuring unit 130 records the measuring signals via the electrodes 7 and/or 7' of the keyboard 3. The analyzer unit 110 performs a pre-processing of all measuring signals. To this effect, the signals pass through a band pass filter in order to filtrate interferences in the area of the net frequency of 50 and 60 Hz, respectively. Furthermore, the signals are subjected to noise suppression. Having passed the analyzer unit 110, the treated signals from the optical measuring unit 100, heat measuring unit 120, impedance measuring unit 130 and ECG unit 132 get into an evaluation unit 140. The evaluation unit 140 serves the task of computing the essential diagnostic parameters from the measured signals. The functions of the evaluation unit 140 are mainly realized by a software running on computer 2. From the measured signals of the impedance measuring unit 130 which have been recorded depending on time, the composition of the examined body tissue (water content, fat content, etc.) is computed at first. From the signals of the optical measuring unit 100, the arterial oxygen saturation and the capillary oxygen saturation—taking the tissue parameters determined from the impedance measurement as a basis—are computed. Furthermore determined from the measured signals of heat measuring unit 120 and from the plethysmographical data that can be derived from the time-dependent impedance measurement are the supply with blood and the arterial temperature. The pulse wave velocity is determined from the signals of the ECG unit 132 and from those of the optical measuring unit 100. Finally, the venous oxygen saturation and further metabolic parameters, especially the local oxygen consumption and the glucose concentration at the measuring spot are computed by means of the evaluation unit 140 based on the results of all computations made before. The computation results are interpreted by means of a diagnostic unit 150. The diagnostic unit 150 which is also implemented as a software on the computer 2 serves for evaluation of the local metabolic parameters computed by means of the evaluation unit 140. To display the measuring results, the evaluation unit 140 and the diagnostic unit 150 are linked to a graphical unit 160 which activates monitor 9. Data gained can be memorized in a memory unit 170, i.e. by simultaneous memorization of the date and time of the relevant measurement. Moreover, an interface unit 180 is provided for which serves to link computer 2 with a data network for transmission of computed physiological parameters. Via the interface 180, all data and parameters, especially the data and parameters memorized in the memory unit 170 can be transmitted to a not precisely shown PC of a physician performing the treatment. There, the data can be analyzed in greater detail. In particular, data and parameters recorded over an extensive period of time with the device 1 can be checked for alterations in order to draw conclusions with regard to the development of an existing disease FIG. 3 illustrates the set-up of the optical measuring unit 100 of the inventive device 1. The optical measuring unit 100 comprises a microcontroller 190. An integral part of microcontroller 190 is a timing generator 200. It generates control signals that are passed on to a modulation unit 210. The temporal modulation of light emission from light-emitting diode 4 is thereby controlled. The light-emitting diode 4 is connected via a control unit 220 to the modulation unit 210. The intensity of the light emitted from light-emitting diode 4 is moreover adaptable via a performance rate control unit 230. The light-emitting diode 4 is capable of emitting light at three different wavelengths at least. For this purpose, various light-emitting semiconductor elements are united in a single casing of light-emitting diode 4. By means of the timing generator 200, the temporal sequence of light emission is controlled at various light wavelengths. The photo sensors 5 integrated into the measuring head 3 of device 1 as well as the light-emitting diode 4 are in contact with the user's body tissue 240 schematically indicated in FIG. 3. In body tissue 240, the light from light-emitting diode 4 is scattered and absorbed according to the oxygen concentration of blood streaming through tissue 240. The scattered light is registered by photo sensors 5. The photoelectric current of each photo sensor 5 is converted by means of a converter 250 into a voltage, amplified by means of an amplifier 260 and converted by means of a digital/analogous transformer 270 into digital measuring signals. The digital signals are then passed on to a demodulator 280 which is an integral part of the microcontroller 190. Demodulator 280 separates picked-up measuring signals by the corresponding light wavelengths. Finally, the signals are passed on to the analyzer unit 110.

Figure 4:
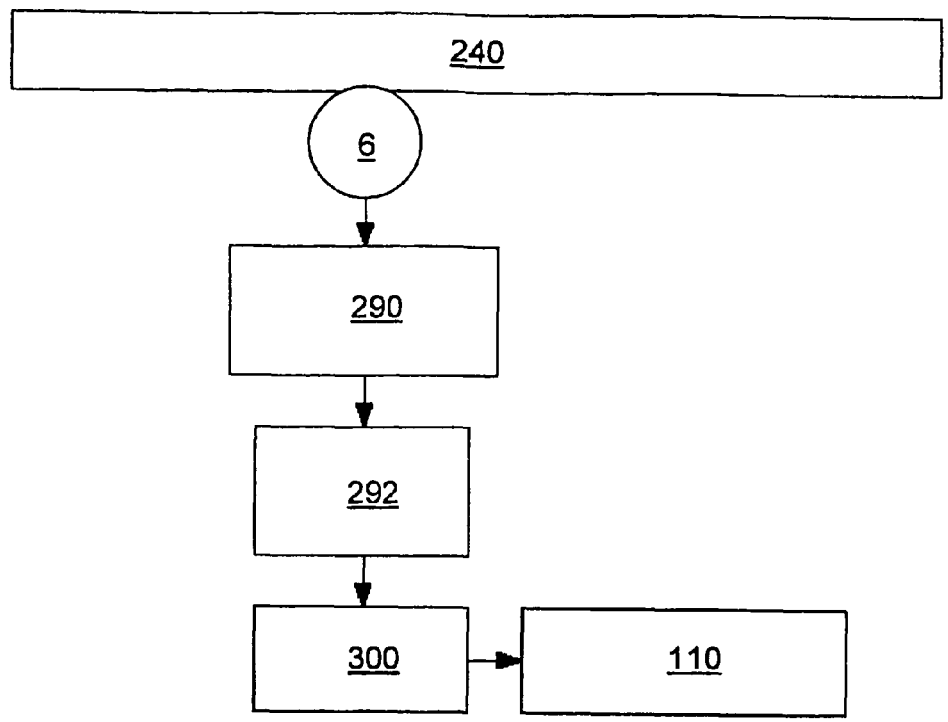
FIG. 4 shows a block diagram representation of the heat measuring unit.

FIG. 4 outlines the set-up of the heat measuring unit 120 of the inventive measuring device. Heat sensor 6 which is in contact with body tissue 240 comprises several temperature measuring elements not shown here more precisely as well as a heat-conducting element. As soon as sensor 6 comes in contact with tissue 240, a heat exchange commences. By means of the temperature measuring elements, the temperature is measured at various spots on the heat-conducting element of sensor 6. Hereof, it is possible to determine the heat locally produced in the tissue 240 (resolved for place, time and depth). The signals recorded by means of the temperature measuring elements pass through an impedance transformer 290 as well as an amplifier 292 and are digitized by means of an analogous/digital transformer 300. The digital measuring signals are then passed on to the analyzer unit 110 for further processing. A suitable heat sensor 6 is described, for example, in the publication by Ok Kyung Cho et al. (Ok Kyung Cho, Yoon Ok Kim, Hiroshi Mitsumaki, Katsuhiko Kuwa, "Noninvasive Measurement of Glucose by Metabolic Heat Conformation Method", Clinical Chemistry 50, 2004, No. 10, P. 1894 to 1898).

Figure 5:
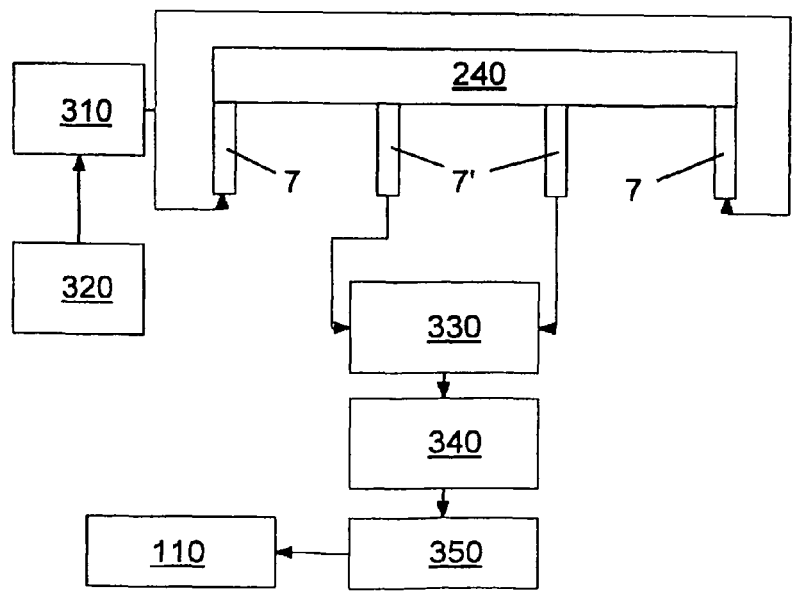
FIG. 5 shows a block diagram representation of the impedance measuring unit of the measuring device.

FIG. 5 outlines the set-up of the impedance measuring unit 130 of the inventive measuring device. The impedance measuring unit 130 is comprised of electrodes 7 and 7'. Via contact surfaces 7, an alternating current generated by power source 310 is impressed onto the examined body tissue 240. The power source 310 is triggered by a sinus generator 320. The frequency of the alternating current varies between 20 kHz and 100 kHz. Via contact surfaces 7, a voltage is picked-up as measuring signal at the body tissue 240. From the ratio of the measured voltage versus the impressed electric current, one can draw a conclusion as to the impedance of the body tissue 240. For this purpose, the voltage is amplified by means of an amplifier 330 and filtered by means of filter 340 in order to eliminate interfering signals. A digitalization is again effected by means of an analogous/digital transformer 350. Digitized measuring values in turn are passed on to the analyzer unit 110 for further processing.

Figure 6:
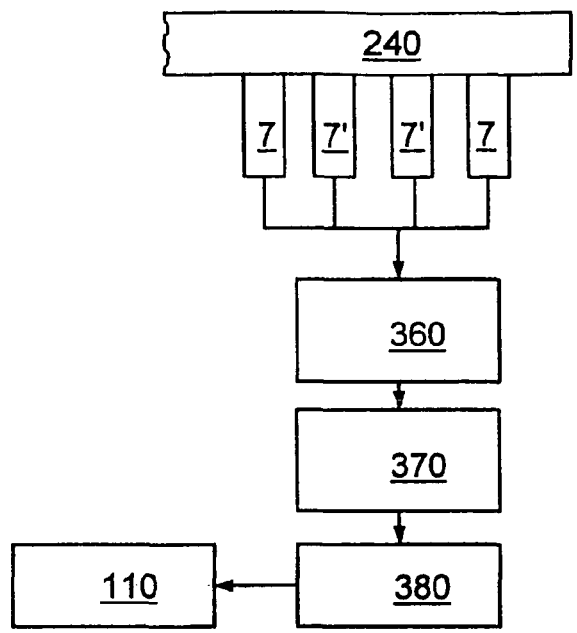
FIG. 6 shows a block diagram representation of the ECG unit of the measuring device.

FIG. 6 outlines the set-up of the ECG unit 132 of the inventive measuring device. The ECG unit 132 captures an ECG signal via ECG electrodes 7. These are the electrodes of the impedance measuring unit 130. The electrodes 7 thus fulfill a twin function in the embodiment example outlined here. A usable two-point derivation of the ECG signal is generated as outlined hereinabove by touching both electrodes 7 with one hand each. The two electrodes 3 are integrated in keyboard 7. Separate electrodes, e.g. electrodes connected via a cable are not required (for a simple two-point derivation of the ECG signal). The derived ECG signal is processed and treated by means of amplifier 360 and filter 370. Having passed another analogous/digital transformer 380, the signal is passed on to the analyzer unit 110.

Figure 7:
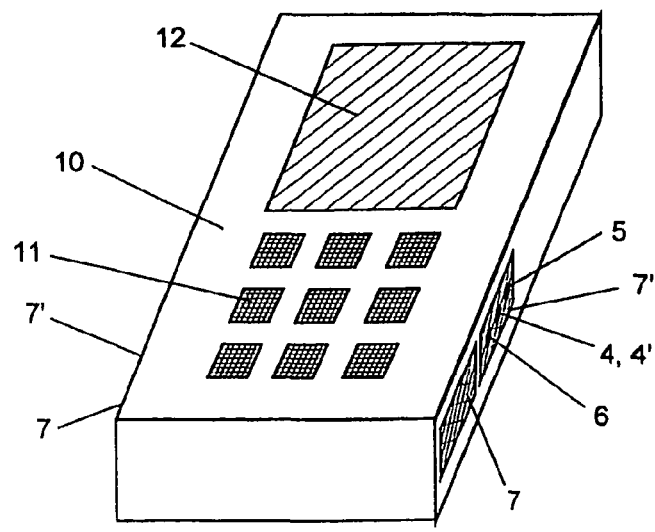
FIG. 7 shows a schematic view of a second embodiment example of the inventive measuring device.

FIG. 7 shows a second embodiment example of the inventive measuring device. The inventive measuring device is comprised of a mobile device 10, i.e. a mobile phone. To be seen at the front side of device 10 are the usual operating keys 11. Integrated into the lateral areas of the casing of the device 10 are various diagnostic measuring sensors. These are touched by a user of the device with the finger to execute a measurement. Integrated into the casing are light sources 4, 4', for example in form of light-emitting diodes that are capable of emitting light at various wavelengths. Furthermore, the device 10 is comprised of one or several photo sensors 5. These photo sensors are arranged in immediate vicinity to the light source 4 and 4', respectively. Sensors 5 receive the light from light source 4 and/or 4' scattered in the tissue at the user's finger tip. Moreover, a heat sensor 6 is provided immediately next to light source 4 and/or 4'. Hereby it is ensured that the determination of blood supply based on heat measurement is accomplished at the same measuring place as the optical measurement. Moreover, a total of four electrodes 7 and/or 7' are provided at the lateral casing surfaces of mobile phone 10 to measure the local bio-electrical impedance. The user of mobile phone 10 touches two electrodes 7 and/or 7' each simultaneously with one hand. One of the two contact surfaces serves to impress an electrical current at the measuring place, while the other contact surface is utilized for voltage measurement. In this manner it is ensured that the measuring results are not influenced by the contact resistance of the measuring electrodes. The two electrodes designated by reference number 7 are also utilized as ECG electrodes of an ECG of the measuring device which is also integrated into the mobile phone 10. The two electrodes each are touched with the finger tips so that a two-point derivation (arm-to-arm measurement) is obtained. The measuring signals recorded by means of various sensors integrated into the mobile phone 10 are processed by means of the (not precisely shown) microprocessor of mobile phone 10. The physiological parameters thus obtained are then indicated on a display 12 of mobile phone 10. For example, the display shows the arterial, capillary and venous oxygen saturation. Furthermore displayed is the determined heart frequency as well as the fat content of tissue. Finally, a blood glucose value is also indicated. The user can determine the physiological parameters being its interest at any time. To this effect the user merely lays the fingers with which he/she would otherwise actuate the keys 11 onto the electrodes 7, 7'. Then the parameters are indicated instantly by means of display 12 after the measuring signals have been processed by means of the microprocessor of mobile phone 10. The function of mobile phone 10 inventively configured as a medical measuring device is mainly based upon the indirect process for non-invasive determination of the blood glucose value as described hereinabove at which the effect of glucose and/or the energy turnover of the physiological reactions in the body initiated by glucose is examined. Reference is made to the relevant description for explanation of the practical example illustrated in FIG. 1. Similarly as with the keyboard 3, the light sources 4, 4' and the sensors 5 need not be arranged directly at the casing surface with the mobile phone 10 either. Instead, the light can be conducted via light-conductive fibres from and/or to the casing surface, with the actual light sources and/or sensors being arranged in the interior of the casing. Several light sources and/or sensors can be coupled to a unique light-conductive fibre.

Figure 8:
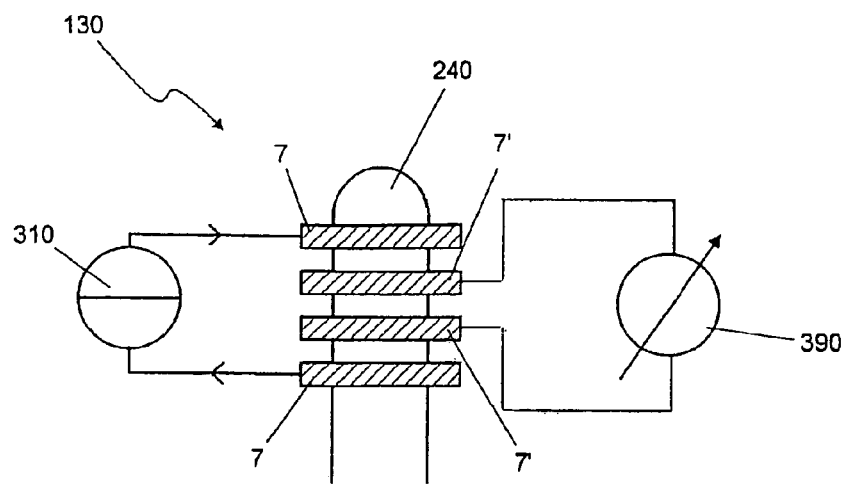
FIG. 8 illustrates the local bio-electrical impedance measurement in accordance with the present invention.

The bio-electrical impedance measuring unit 130 of the inventive measuring device as illustrated in FIG. 8 comprises two electrodes 7 for the supply of electrical alternating current from power source 310 with a variable frequency for the determination of local resistance and local reactance as well as two or more measuring electrodes 7' for the impedance measurement of the body tissue 240, in the area of the finger of the user of the device. On account of the four-point measurement, transitory resistances between electrodes 7, 7' and the body tissue 240 do not falsify the measurement. Expediently, the distance between electrodes 7, 7' may amount to just a few millimeters up to a few centimeters. Generating an alternating current of variable frequency by means of power source 310 is advantageous, because it is possible to measure the complex impedance in this manner. The measuring signal is captured by means of a voltmeter 390. The measuring signal is expediently digitized by means of an analogous/digital transformer (not shown in FIG. 8) and then subjected to a discrete Fourier transformation (DFT). The DFT algorithm then supplies the real and the imaginary part of impedance. On account of the small electrode distance, the impedance measuring unit 130 shown here can be of a very compact set-up and thus be well integrated into a mobile electronic device (e.g. a wristwatch, mobile phone, MP3 player, digital camera, etc.).

Figure 9:
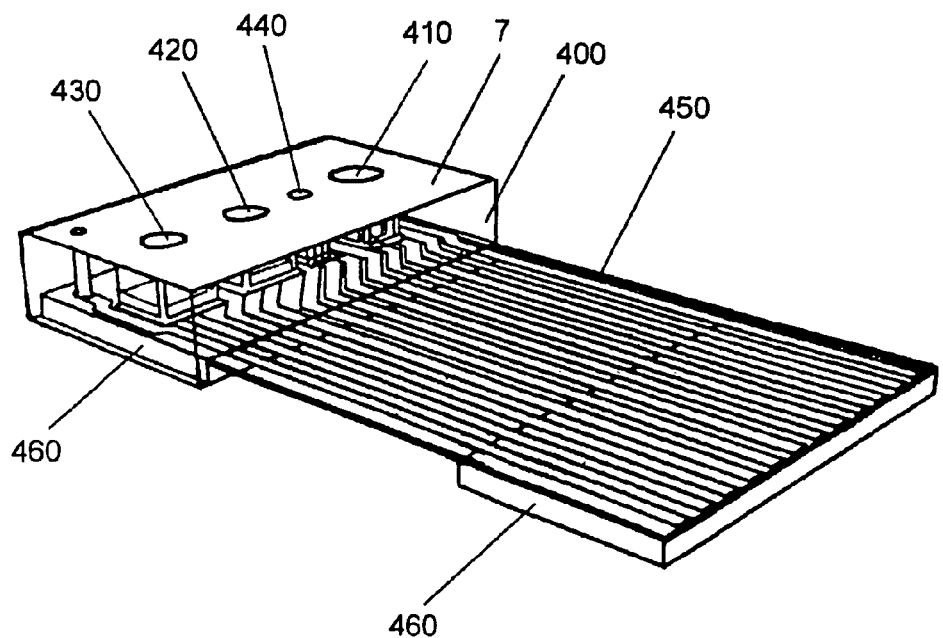
FIG. 9 illustrates the diagnostic sensoric unit of the inventive measuring device.

FIG. 9 illustrates the design and set-up of the diagnostic sensoric unit of the inventive measuring device. The various measuring units of the sensor unit are integrated into a sensor casing 400 having very small outer dimensions. Arranged at the upper side of the casing 400 is a planar ECG electrode 7 which is comprised of a thin, electrically conductive foil. On installing the sensor unit into a computer keyboard or into a mobile appliance, the sensor casing 400 is so arranged that the user can touch the ECG electrode 7 and another electrode (not shown in FIG. 9) with various extremities for ECG derivation. In a sensible manner the ECG electrode is a thin stainless steel foil. The small construction module of the micro-casing sized 5 mm (W)×8 mm (L)×1.8 mm (H) (with the illustrated practical example) allows for a flexible and low-cost installation of the sensor unit into different casings of various appliances obtainable on the market. To enable a simultaneous determination of the oxygen saturation in arterial blood, an optical measuring unit, i.e. a pulsoximeter, is integrated into the sensor casing 400. It is comprised of two or several optical radiation sources, the radiation of which can pass through a recess 410 in the ECG electrode 7. Moreover, the pulsoximeter is comprised of two optical radiation sensors, e.g. in form of photo diodes. The light scattered in the body tissue (e.g. of a finger imposed on the electrode 7) falls through two recesses 420 and 430 in the electrode 7 onto the radiation sensors. The recesses 420 and 430 are arranged at a different distance to the recess 410. In the sensor unit, the light from two or several optical radiation sources (e.g. light-emitting diodes) within the casing 400 is coupled into a light-conducting fibre or into a suitable light-conducting body so that there is only one recess 410 for all radiation sources and the light from all radiation of the sensor unit is conducted at the same spot into the body tissue to be examined. The photo diodes each are individually coupled to one optical fibre or to a suitably configured light-conducting body. The optical measuring unit allows for a simultaneous measurement of the oxygen saturation of the blood circulating in the examined body tissue and of the volume pulse. In a sensible manner, not only light-emitting diodes but also other radiation sources, e.g. vertical cavity surface emitting lasers (VCSEL) are utilized for this purpose. A temperature sensor, namely a thermistor, is integrated into the sensor casing to enable a simultaneous determination of the thermal properties of the examined tissue. Another recess 440 is provided for it in the ECG electrode 7. The thermistor in the sensor casing 400 is so arranged that it has good thermal contact to the examined body tissue. With the illustrated practical example, the thermistor is located between the recess 410 for the light-conducting fibre of the optical radiation sources and the recess 420 for the light-conducting fibre of the first photo diode. The sensor unit can be supplemented with an impedance measuring unit without any difficulties. To this effect, at least one additional planar electrode (not shown in FIG. 9) must be configured at the upper side of the sensor casing 400 to serve as feeder or measuring electrode of the impedance measuring unit. In a sensible manner, the same measuring electrodes can be utilized for capturing the bio-impedance signal and the ECG signal. For the electrical contact of the sensor unit (e.g. with the electronics of a mobile phone), the sensor casing 400 with all the integrated measuring units is directly mounted on a ribbon cable 450 with a suitable conductor routing so that a simple electrical installation of the sensor unit is possible with the aid of the ribbon cable 450. The ribbon cable 450 may have stiffeners 460 at suitable spots to improve stability.

The invention claimed is:

1. A measuring device for non-invasive determination of at least one physiological parameter, said measuring device comprising:
   (a) diagnostic sensor unit configured to generate measuring signals, said diagnostic sensor unit being integrated into or connectible to a computer, to a peripheral component of a computer, or to a mobile device of entertainment or communication technology, and
   (b) an evaluation unit comprising a computer processor configured to process the measuring signals,
   wherein the diagnostic sensor unit comprises:
   an optical measuring unit configured to generate a volume pulse signal, said optical measuring unit comprising at least two radiation sources configured to irradiate examined body tissue and at least two radiation sensors configured to detect radiation scattered by or transmitted from the examined body tissue, with the at least two radiation sensors being arranged at a different distance to a first radiation source of the at least two radiation sources, and
   an ECG unit configured to capture an ECG signal via two or more ECG electrodes,
   wherein the diagnostic sensor unit comprises at least one device selected from the group consisting of:
   a temperature sensor or a heat sensor,
   a contact pressure sensor, and
   a bio-electrical impedance measuring unit, and
   wherein the evaluation unit is configured to evaluate a chronological course of the volume pulse signal and the ECG signal to determine a corrective factor and to determine local glucose concentration from the corrective factor and the measuring signals generated via the optical measuring unit and the at least one device selected from the group.

2. The measuring device as defined in claim 1, wherein the at least two radiation sources have different spatial radiation characteristics.

3. The measuring device as defined in claim 1, wherein the evaluation unit is configured to determine at least one of local oxygen consumption and blood glucose level based on intensities of the radiation from the at least two radiation sources scattered by or transmitted from the examined body tissue.

4. The measuring device as defined in claim 1, wherein the diagnostic sensor unit comprises a bio-electrical impedance measuring unit, and wherein the bio-electrical impedance measuring unit comprises one pair of feeder electrodes to supply electrical alternating current and one pair of measuring electrodes for impedance measurement, with the distance between the pair of feeder electrodes and the pair of measuring electrodes amounting to less than 10 cm.

5. The measuring device as defined in claim 1, wherein the evaluation unit is furthermore configured to determine blood glucose level from the local glucose concentration.

6. The measuring device as defined in claim 1, further comprising a diagnostic unit for evaluation of the at least one physiological parameter determined via the evaluation unit, with functions of the diagnostic unit being realized by a software.

7. The measuring device as defined in claim 1, wherein the measuring device further comprises a display unit for display of determined physiological parameters.

8. The measuring device as defined in claim 1, wherein the measuring device is configured to transmit the measuring signals or to transmit the at least one physiological parameter via a data net or a communication net.

9. The measuring device as defined in claim 1, wherein the diagnostic sensor unit is integrated into or connectible to a computer or to a mobile device of entertainment or communication technology, and wherein the computer or the mobile device is configured to transmit the measuring signals or to transmit the at least one physiological parameter via a data net or a communication net.

10. The measuring device as defined in claim 1, wherein the diagnostic sensor unit is integrated into or connectible to a peripheral component of a computer, wherein the peripheral component is a keyboard, and wherein said computer is a mobile device selected from the group consisting of a notebook computer, a laptop computer, a palmtop mobile device and a handheld mobile device.

11. The measuring device as defined in claim 1, wherein the diagnostic sensor unit comprises the temperature sensor, said temperature sensor determining ambient temperature in an environment of the measuring device.

12. The measuring device as defined in claim 11, further comprising another temperature sensor for determination of body core temperature.

13. The measuring device as defined in claim 1, wherein the evaluation unit is configured to determine breathing frequency from the measuring signals of the diagnostic measuring unit.

14. The measuring device as defined in claim 1, wherein said diagnostic sensor unit is integrated into or connectible to a mobile device of entertainment or communication technology, wherein the diagnostic sensor unit forms a unit separated from the mobile device, and wherein the diagnostic sensor unit comprises a cordless or cord-bound signal line for connection to the mobile device.

15. The measuring device as defined in claim 1, wherein the diagnostic sensor unit comprises a unit for the analysis of samples.

16. The measuring device as defined in claim 1, wherein the diagnostic sensor unit comprises a temperature sensor or a heat sensor, wherein the optical measuring unit and the temperature sensor or the heat sensor are arranged in a common sensor casing, and wherein one of the ECG electrodes is a planar ECG electrode configured at an upper side of the sensor casing and having at least one recess to allow for passage of radiation emitted from the at least one radiation source.

17. The measuring device as defined in claim 16, wherein the at least one radiation source, the at least one radiation sensor and the temperature sensor or the heat sensor are arranged on a common substrate within the sensor casing.

18. The measuring device as defined in claim 16, wherein the sensor casing has dimensions of less than 1 cm×1 cm×1 cm.

19. The measuring device as defined in claim 16, wherein the diagnostic sensor unit comprises a bio-electrical impedance measuring unit, and wherein at least one additional planar electrode is configured at the upper side of said sensor casing, said at least one additional planar electrode serving as feeder or measuring electrode of the bio-electrical impedance measuring unit.

20. The measuring device as defined in claim 1, further comprising a blood pressure measuring unit for measurement of at least one of systolic blood pressure and diastolic blood pressure.

21. The measuring device as defined in claim 1, wherein said diagnostic sensor unit is integrated into or connectible to a peripheral component of a computer, wherein said peripheral component is a keyboard, wherein said diagnostic sensor unit comprises a contact pressure sensor, wherein said contact pressure sensor is configured to measure contact pressure of a finger on the at least one radiation sensor, and wherein the evaluation unit is configured to evaluate a chronological course of the ECG signal.

22. The measuring device as defined in claim 1, wherein the computer processor of the evaluation unit is a computer processor of the computer or of the mobile device.

23. The measuring device as defined in claim 1, wherein the at least two radiation sources are configured to irradiate different volume ranges of the examined body tissue.

24. The measuring device as defined in claim 7, wherein the diagnostic sensor unit is integrated into or connectable to a peripheral of a computer or to a mobile device of entertainment or communication technology, and wherein the display unit is a display unit of the peripheral of the computer or of the mobile device.

25. The measuring device as defined in claim 1, wherein the diagnostic sensor unit comprises a bio-electrical impedance unit comprising a first impedance electrode, and wherein at least one electrode is one of the two or more ECG electrodes and is also the first impedance electrode.

* * * * *